United States Patent
Oda

(10) Patent No.: US 9,047,661 B2
(45) Date of Patent: Jun. 2, 2015

(54) SYSTEM AND METHOD FOR RADIOGRAPHING INFORMATION MANAGEMENT FOR LOW-DOSE RADIOGRAPHING AND RECORDING MEDIUM STORING PROGRAM THEREFOR

(71) Applicant: FUJIFILM Corporation, Tokyo (JP)

(72) Inventor: Yasufumi Oda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 121 days.

(21) Appl. No.: 13/800,816

(22) Filed: Mar. 13, 2013

(65) Prior Publication Data

US 2013/0243300 A1     Sep. 19, 2013

(30) Foreign Application Priority Data

Mar. 19, 2012   (JP) ................................ 2012-062099

(51) Int. Cl.
| | |
|---|---|
| G06K 9/00 | (2006.01) |
| G06T 7/00 | (2006.01) |
| G06F 19/00 | (2011.01) |
| A61B 6/00 | (2006.01) |

(52) U.S. Cl.
CPC ............ *G06T 7/0012* (2013.01); *G06F 19/321* (2013.01); *G06F 19/327* (2013.01); *G06F 19/3481* (2013.01); *A61B 6/4233* (2013.01); *A61B 6/5294* (2013.01); *A61B 6/542* (2013.01); *A61B 6/563* (2013.01); *A61B 6/581* (2013.01); *A61B 6/582* (2013.01); *A61B 6/586* (2013.01)

(58) Field of Classification Search
None
See application file for complete search history.

(56) References Cited

U.S. PATENT DOCUMENTS

| | | | |
|---|---|---|---|
| 6,282,513 B1 * | 8/2001 | Strawder | 705/2 |
| 6,801,647 B1 * | 10/2004 | Arakawa | 382/132 |
| 8,019,625 B2 * | 9/2011 | Minnigh et al. | 705/3 |
| 2005/0209888 A1 * | 9/2005 | Oowaki et al. | 705/3 |
| 2006/0004870 A1 * | 1/2006 | Pomeroy et al. | 707/104.1 |
| 2007/0036268 A1 * | 2/2007 | Matsuno | 378/98.2 |
| 2008/0306760 A1 * | 12/2008 | Minnigh et al. | 705/2 |
| 2013/0243300 A1 * | 9/2013 | Oda | 382/132 |

FOREIGN PATENT DOCUMENTS

| | | |
|---|---|---|
| JP | 2006-150033 A | 6/2006 |
| JP | 2007-143719 A | 6/2007 |

OTHER PUBLICATIONS

Japanese Office Action and English translation thereof, dated Mar. 5, 2014, for Japanese Application No. 2012-062099.

* cited by examiner

*Primary Examiner* — Tahmina Ansari
(74) *Attorney, Agent, or Firm* — Birch, Stewart, Kolasch & Birch, LLP

(57) ABSTRACT

Useful material for making low-dose radiographing and an increase in the image quality compatible with each other is provided. An image analysis unit of a central server derives the granularity of a region of interest by analyzing an X-ray image transmitted from a client terminal. A storage processing unit stores the granularity, the X-ray image, and radiographing information in a storage device so as to be associated with each other. A search processing unit searches for the radiographing information, which is matched with search conditions designated from the client terminal, and granularity, which is associated with the radiographing information, from the storage device. A statistical data generation unit generates a scatter plot, which has granularity on the vertical axis and a radiation dose on the horizontal axis, as statistical data. The statistical data is transmitted to the client terminal and is displayed on a display of the client terminal.

15 Claims, 13 Drawing Sheets

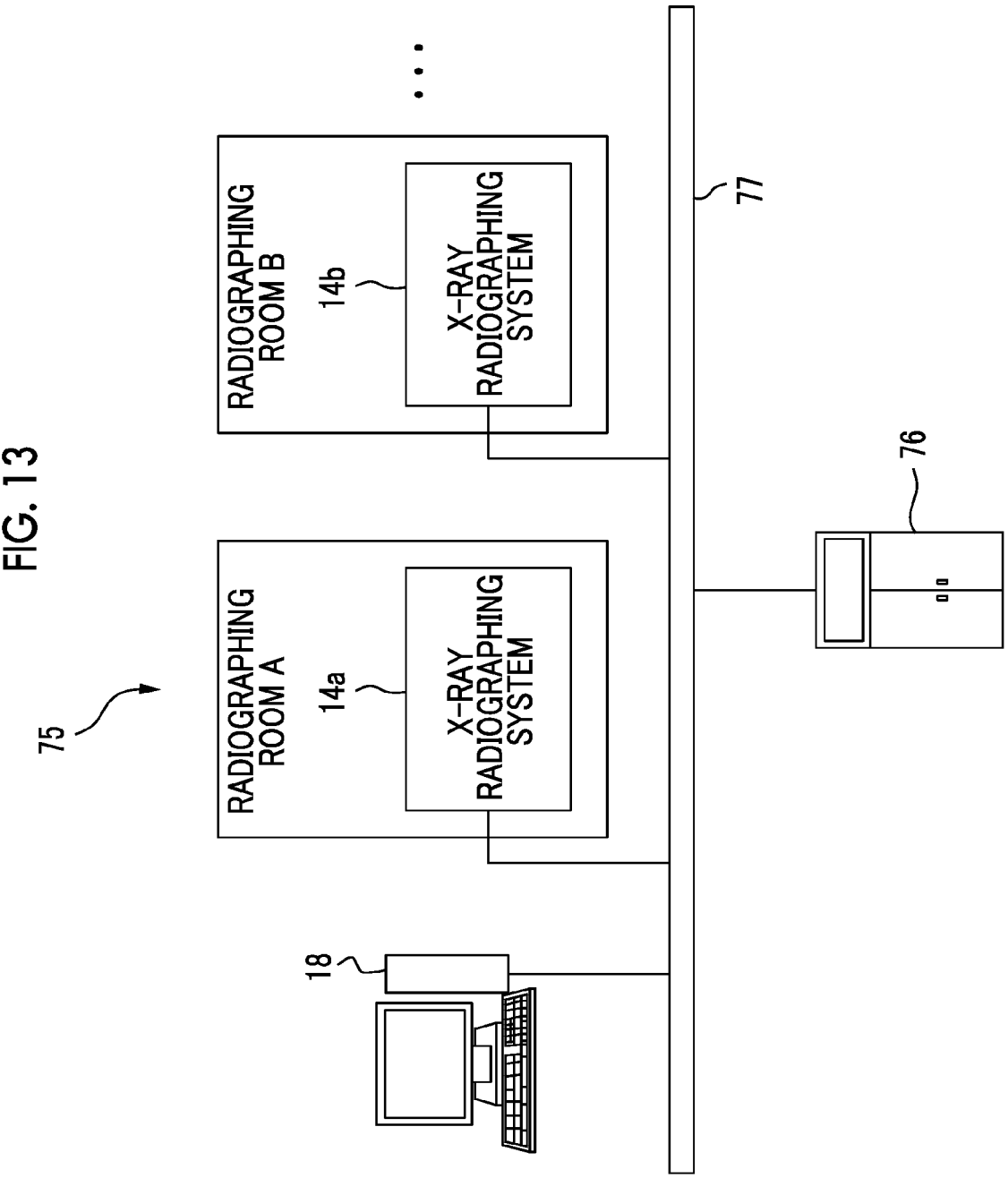

SYSTEM AND METHOD FOR RADIOGRAPHING INFORMATION MANAGEMENT FOR LOW-DOSE RADIOGRAPHING AND RECORDING MEDIUM STORING PROGRAM THEREFOR

BACKGROUND OF THE INVENTION

1. Field of the Invention

The present invention relates to a system and method for radiographing information management, which manages radiographing information and provides support services for low-dose radiographing, and a non-transitory computer-readable recording medium that records a radiographing information management program.

2. Description of the Related Art

In the medical field, X-ray radiographing systems using radiation, for example, X-rays are known. In the field of recent X-ray radiographing systems, an X-ray image detection device that uses a flat panel detector (FPD) as a detection panel instead of an X-ray film or an imaging plate (IP) has become widespread. An electronic cassette (portable X-ray image detection device) in which an FPD is built into the housing having a rectangular parallelepiped shape has already been put to practical use.

The sensitivity of the X-ray image detection device has improved with the development of such a detection panel. As a result, the same X-ray image or a clearer image than in the related art can be obtained with a low radiation dose. In addition, with recent demands for reducing the dose of exposure to the patient and an increase in the sensitivity of the X-ray image detection device, medical facilities are also required to perform radiographing with a radiation dose as low as possible.

JP2006-150033A discloses a system that stores and manages dose information, which is transmitted from X-ray radiographing systems of a plurality of medical facilities or radiographing rooms, in time series and provides various kinds of information that may be of assistance to low-dose radiographing. JP2006-150033A discloses providing and displaying a list of radiographing conditions, which are recommended by other medical facilities or a manufacturer for the same radiographing part or examination purpose and patients being approximately the same age or having approximately the same weight, for the user. In this case, a radiation dose index of the radiographing conditions and an image quality index of an X-ray image are displayed in a list. When one of the radiographing conditions is selected, details thereof are displayed together with the radiographing conditions of the own facility. In addition, JP2006-150033A also discloses that the selected radiographing condition can be copied to the own facility.

SUMMARY OF THE INVENTION

Since image quality degrades as a radiation dose is decreased in order to reduce the amount of exposure to the patient, trade-offs are made between the quality of an X-ray image and the X-ray dose. For this reason, in order to realize low-dose radiographing without degrading the quality of an X-ray image as much as possible, optimizing the radiographing conditions by trial and error is required, and this takes enormous time and effort. For this reason, rather than each medical facility trying to optimize the radiographing conditions alone, it is effective for each medical facility to adopt radiographing conditions of other medical facilities, which have optimized the radiographing conditions so that low-dose radiographing and an increase in the quality of an X-ray image are compatible with each other, as a model and make efforts to optimize the radiographing conditions based on the adopted radiographing conditions, and an added benefit is that it saves time.

JP2006-150033A discloses that low-dose radiographing and the increase in the quality of an X-ray image are compatible with each other by displaying the radiation dose index and the image quality index of the radiographing conditions in a list. However, it is difficult to intuitively understand the relationship between the own facility and other facilities in such a list display. For this reason, it takes time to compare the radiographing conditions of the own facility with the radiographing conditions of the other facilities, and there is a high possibility of an occurrence of a mistake, such as overlooking the radiographing conditions in which low-dose radiographing and an increase in the image quality can be optimized or selecting the radiographing conditions in which neither low-dose radiographing nor an increase in the image quality is satisfactorily realized.

The present invention has been made in view of the above-mentioned problems and an object of the present invention is to provide a system and method for radiographing information management, which can provide useful materials for making low-dose radiographing and an increase in the image quality compatible with each other, and a non-transitory computer-readable recording medium that records a radiographing information management program.

In order to achieve the above-described object, according to an aspect of the present invention, there is provided a radiographing information management system including: an image analysis unit that analyzes a radiological image, which is obtained by a radiographing system, to derive an image quality evaluation value indicating quality of the image; a storage processing unit that stores the image quality evaluation value derived by the image analysis unit and radiographing information, which includes an item of a radiation dose or an equivalent amount equivalent to the radiation dose, in a storage unit so as to be associated with each other; a search unit that searches for radiographing information, which has an item designated in search conditions, and an image quality evaluation value, which is associated with the radiographing information, from the storage unit; a statistical data generation unit that generates statistical data, which has an image quality evaluation value and a radiation dose or an equivalent amount as parameters, based on the radiographing information and the image quality evaluation value associated with the radiographing information that have been searched for by the search unit; and a display unit that displays the statistical data generated by the statistical data generation unit.

The radiographing information includes any one of a medical facility in which a radiographing system is placed, a radiographer in charge of radiographing, and a radiographing room where radiographing is performed. The statistical data generation unit generates a scatter plot including a set of points, which indicates a relationship between the image quality evaluation value and the radiation dose or the equivalent amount for each medical facility, each radiographer, or each radiographing room, as the statistical data. An approximated curve of a scatter plot may be calculated, and this may be generated as statistical data. When there are two image quality evaluation values, a three-dimensional contour plot may be generated as statistical data.

The radiographing information includes an item of information of a patient, who has been subject to radiographing, and this information may be designated as search conditions. The patient information includes any one of age, sex, and body type, for example.

In addition, the radiographing information includes an item of information of the radiographing system, and this information may be designated as search conditions. The system information is information of IDs for uniquely identifying a radiological image detection device, a grid, and a filter and information indicating whether settings of a collimator and a filter are automatic or manual, for example.

When IDs of a plurality of radiological image detection devices are designated as the search conditions, the statistical data generation unit generates statistical data of each of the radiological image detection devices, and the display unit displays the statistical data of the radiological image detection devices so as to be able to be compared with each other.

In addition, the radiographing information includes an item of radiographing conditions, and this may be designated as search conditions. The radiographing conditions include a radiographing part, a tube voltage, a tube current, and irradiation time of a radiation source, and a distance between a radiation source and a radiological image detection device, for example.

The display unit displays a plurality of radiographing conditions so as to be able to be compared with each other. In addition, the display unit displays radiographing conditions so as to be linked to statistical data. For example, when a certain point of statistical data is selected, radiographing conditions of the point are displayed.

The display unit displays a GUI (Graphical User Interface) for copying radiographing conditions. Preferably, a warning display unit that, when system information of radiographing information of a copy location having the copied radiographing conditions is different from information of a radiographing information system of a copy receiving side, displays this situation is further provided.

The image quality evaluation value is granularity of a region of interest of a radiological image. Instead of the granularity or in addition to the granularity, contrast and sharpness may be adopted.

According to another aspect of the present invention, there is provided a radiographing information management method including: an image analysis step of analyzing a radiological image, which is obtained by a radiographing system, to derive an image quality evaluation value using an image analysis unit; a storage processing step of storing the image quality evaluation value derived in the image analysis step and radiographing information, which includes an item of a radiation dose or an equivalent amount equivalent to the radiation dose, in a storage unit so as to be associated with each other using a storage processing unit; a search step of searching for the radiographing information, which has an item designated in search conditions, and an image quality evaluation value, which is associated with the radiographing information having the item designated in the search conditions, from the storage unit using a search unit; a statistical data generation step of generating statistical data, which has an image quality evaluation value and a radiation dose or an equivalent amount equivalent to the radiation dose as parameters, based on the radiographing information searched for in the search step and the image quality evaluation value associated with the radiographing information searched for in the search step using a statistical data generation unit; and a display step of displaying the statistical data generated in the statistical data generation step on a display unit.

According to still another aspect of the present invention, there is provided a non-transitory computer-readable recording medium that records a radiographing information management program causing a computer to realize: an image analysis function of analyzing a radiological image, which is obtained by a radiographing system, to derive an image quality evaluation value; a storage processing function of storing the image quality evaluation value derived by the image analysis function and radiographing information, which includes an item of a radiation dose or an equivalent amount equivalent to the radiation dose, in a storage unit so as to be associated with each other; a search function of searching for the radiographing information, which has an item designated in search conditions, and an image quality evaluation value, which is associated with the radiographing information having the item designated in the search conditions, from the storage unit; a statistical data generation function of generating statistical data, which has an image quality evaluation value and a radiation dose or an equivalent amount equivalent to the radiation dose as parameters, based on the radiographing information searched for by the search function and the image quality evaluation value associated with the radiographing information searched for by the search function; and a display function of displaying the statistical data generated by the statistical data generation function.

According to the present invention, since statistical data having an image quality evaluation value and a radiation dose or the equivalent amount is generated and displayed, useful material for making low-dose radiographing and an increase in the image quality compatible with each other can be provided.

BRIEF DESCRIPTION OF THE DRAWINGS

FIG. 13 is a diagram showing an example where an X-ray radiographing information management system is built in a single medical facility.

DESCRIPTION OF THE PREFERRED EMBODIMENTS

Figure 1:
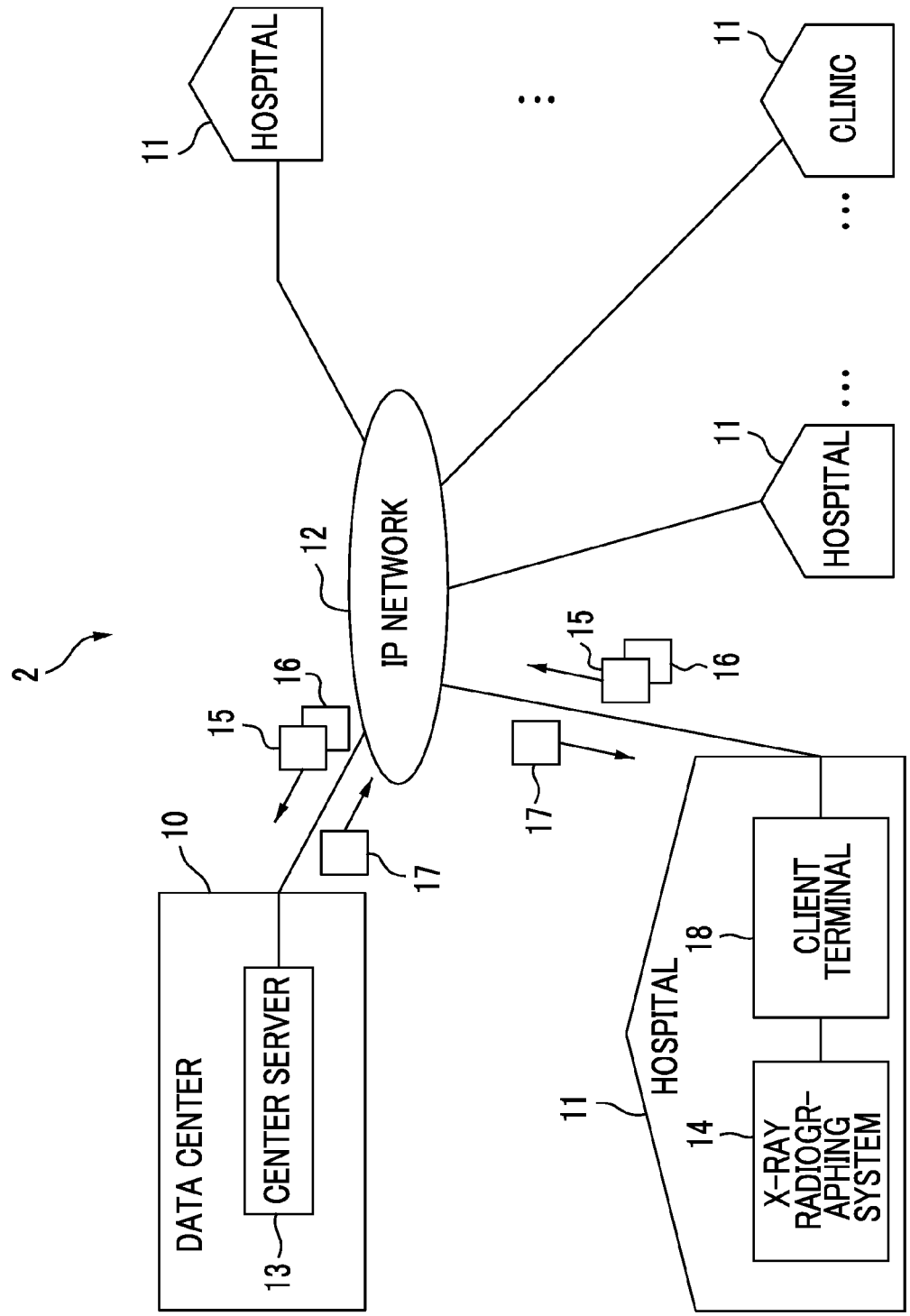
FIG. 1 is a schematic diagram showing the configuration of an X-ray radiographing information management system.

In FIG. 1, an X-ray radiographing information management system 2 is configured to include a data center 10 and a plurality of medical facilities 11. The data center 10 and each of the medical facilities 11 are connected to each other through an IP network 12. Since a dedicated wide area IP network owned by a communication service provider is used as a base network, the IP network 12 is a closed network obtained by constructing a VPN (Virtual Private Network) on the wide area IP network. Due to the VPN, information transmitted through the IP network 12 does not leak to the outside of the X-ray radiographing information management system 2, and the security of information is ensured.

A central server 13 is provided in the data center 10. The central server 13 stores and manages radiographing information 16 and an X-ray image 15 radiographed by an X-ray radiographing system 14 placed in each medical facility 11, generates statistical data 17 based on the X-ray image 15 and the radiographing information 16, and distributes the statistical data 17 to each of the medical facilities 11 to provide support services for low-dose radiographing to each medical facility 11.

The medical facilities 11 include relatively large hospitals, such as university hospitals, and relatively small hospitals, such as privately owned clinics. The X-ray radiographing system 14 and a client terminal 18 are placed in each medical facility 11. The X-ray radiographing system 14 and the client terminal 18 are connected to each other through a LAN placed in the medical facility 11 (refer to FIG. 13).

The X-ray radiographing system 14 has a known configuration including an X-ray source that emits X-rays, an X-ray image detection device that detects X-rays transmitted through a subject and outputs an X-ray image, a control device that controls their operations, a standing radiography platform, and a recumbent radiography platform. A filter to cut soft X-rays is set automatically or manually in the X-ray source, and a grid for removing scattered X-rays is set automatically or manually in each radiography platform. In addition, the X-ray radiographing system 14 has a dose detection sensor that detects the dose of irradiated X-rays.

The client terminal 18 transmits (uploads) the X-ray image 15 and the radiographing information 16 to the central server 13 and also receives (downloads) the statistical data 17 from the central server 13. The X-ray image 15 and the radiographing information 16 may be transmitted each time radiographing is performed by the X-ray radiographing system 14, or the X-ray image 15 and the radiographing information 16 of a predetermined period, such as one day or one week, may be stored in the client terminal 18 and may be collectively transmitted. Alternatively, a cyclic monitoring function may be set in the central server 13, so that the central server 13 checks that the X-ray image 15 and the radiographing information 16 have been uploaded to the client terminal 18 and the X-ray image 15 and the radiographing information 16 are automatically transmitted by the client terminal 18.

Figure 2:
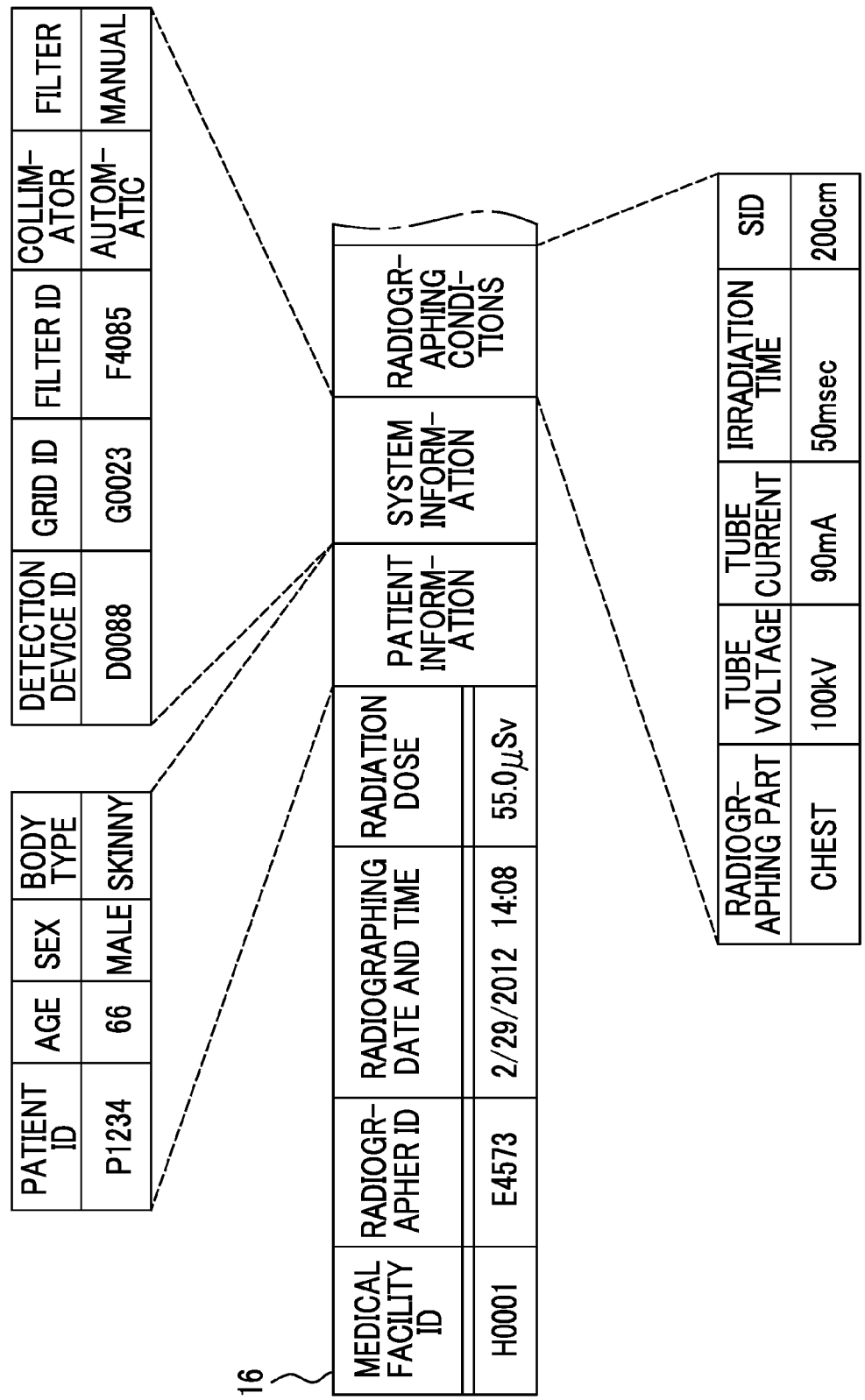
FIG. 2 is a diagram showing each item of radiographing information.

In FIG. 2, the radiographing information 16 includes items, such as an ID of the medical facility 11 in which the X-ray radiographing system 14 is placed, an ID of a radiographer in charge of radiographing, radiographing date and time, a radiation dose detected by the dose detection sensor, patient information, system information, and radiographing conditions. The patient information includes items, such as an ID, age, sex, and body type (skinny, average, obese) of a patient subjected to X-ray radiographing. The system information includes items, such as an ID of an X-ray image detection device used in radiographing, a grid ID, a filter ID, and items indicating whether settings of a collimator and a filter that specify the X-ray irradiation field are automatic or manual. In addition, the radiographing conditions include items, such as a radiographing part, a tube voltage and a tube current of an X-ray source, X-ray irradiation time, and a distance (SID) between an X-ray source and an X-ray image detection device. These items are automatically collected into the client terminal 18 from various medical systems (for example, HIS (Hospital Information System) or RIS (Radiation Information System)) in the medical facility 11, which manage patient information or information related to the radiographing, or manually input.

The medical facility ID is issued from the data center 10 when the data center 10 and each medical facility 11 have a service contract. The radiographer ID and the patient ID are similarly issued from the data center 10. The medical facility ID, the radiographer ID, and the patient ID uniquely identify the medical facility 11, a radiographer, and a patient, respectively.

The detection device ID is information for uniquely identifying the X-ray image detection device, such as the type of the X-ray image detection device, a serial number, a part number, and a lot number. According to this detection device ID, the type of an X-ray image detection device, such as a CR cassette or a DR cassette, sensitivity to X-rays, whether the device is of a TFT type or a CMOS type or whether the device is of a direct conversion type or an indirect conversion type in the case of the DR cassette, which type of material is used to form a scintillator in the case of the indirect conversion type, and the like can be checked. The grid ID and the filter ID are the same as the detection device ID. The information of the type of the X-ray image detection device may be added to the detection device ID, or may be added as a separate item from the detection device ID.

Each of the central server 13 and the client terminal 18 is configured by installing a control program, such as an operating system, or an application program, such as a server program or a client program, on a computer as a base, such as a computer for a server, a workstation, or a personal computer.

Figure 3:
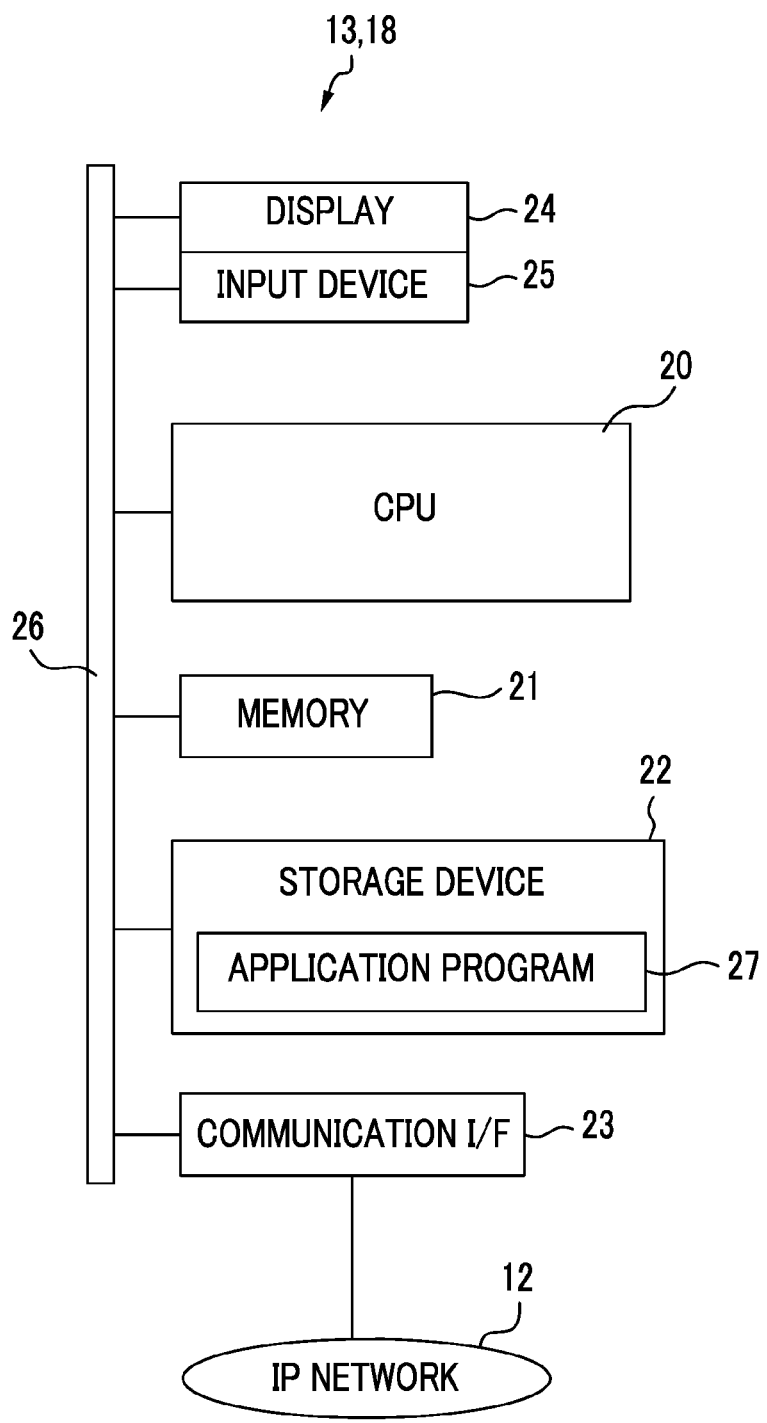
FIG. 3 is a block diagram showing a computer which forms each of a central server and a client terminal.

In FIG. 3, the basic configurations of computers that configure the central server 13 and the client terminal 18 are approximately the same, and each computer includes a CPU 20, a memory 21, a storage device 22, a communication I/F 23, a display 24, and an input device 25. These are connected to each other through a data bus 26.

The storage device 22 is an HDD (Hard Disk Drive) in the case of the client terminal 18, and is a disk array formed by connecting a plurality of HDDs in the case of the central server 13. A control program or an application program 27 is stored in the storage device 22. A server program to execute processing in response to the request from the client terminal 18 and send a notification of the processing result is installed in the central server 13 as the application program 27. A client program to perform processing for transmitting the X-ray image 15 and the radiographing information 16 or statistical data display processing is installed in the client terminal 18 as the application program 27.

The memory 21 is a work memory required when the CPU 20 executes processing. The CPU 20 performs overall control of each unit of the computer by loading the control program stored in the storage device 22 to the memory 21 and executing the processing according to the program. The communication I/F 23 is a network interface that performs data transmission control between the central server 13 and the client terminal 18 through the IP network 12. The input device 25 is a keyboard or a mouse or a touch panel united with the display 24. In addition, in the following explanation, for the sake of distinction, S is added after the numbers of the CPU 20, the storage device 22, and the like corresponding to the central server 13, and C is added after the numbers of the CPU 20, the storage device 22, and the like corresponding to the client terminal 18.

Figure 4:
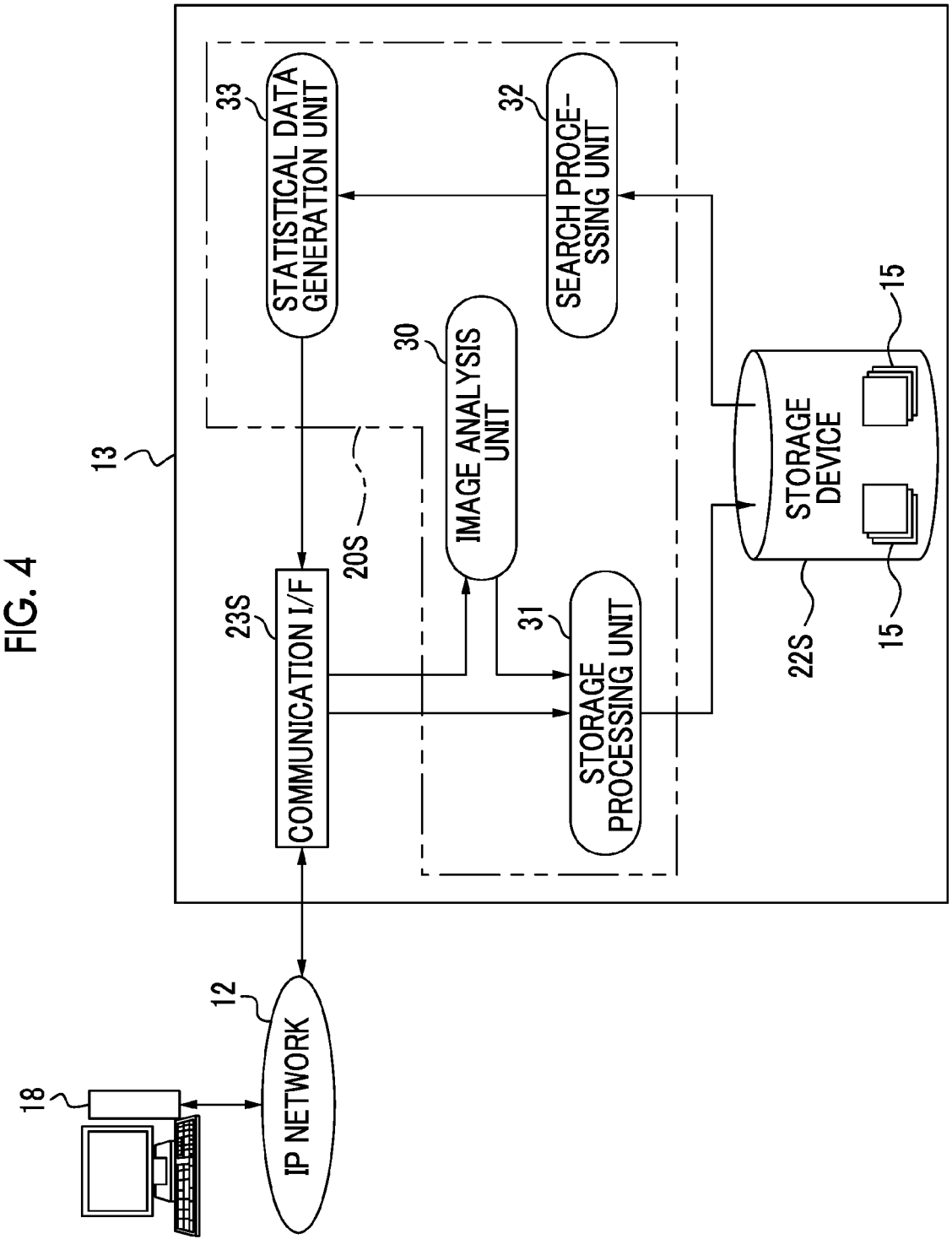
FIG. 4 is a block diagram showing the internal configuration of a central server.

In FIG. 4, when a server program is started, the CPU 20S of the central server 13 functions as an image analysis unit 30 (an aspect of an image analysis unit), a storage processing unit 31 (an aspect of a storage processing unit), a search processing unit 32 (an aspect of a search unit), and a statistical data generation unit 33 (an aspect of a statistical data generation unit).

The image analysis unit 30 analyzes the X-ray image 15 from the client terminal 18 of each medical facility 11, which has been received through the communication I/F 23S, and derives the granularity (degree of roughness) of the region of interest as an image quality evaluation value. The image analysis unit 30 transmits the derived granularity to the storage processing unit 31. The region of interest may be set in advance for each radiographing part. For example, in the case of a chest, regions corresponding to the left and right lung areas may be set as the region of interest. Alternatively, the region of interest may also be a pixel region (region around a reading sensitivity value (S value)) having a gradation value of the central value ±α of a gradation value determined by analyzing the X-ray image 15 using a histogram. In addition, when the gradation value is expressed in 10 bits of 0 to 1023, the central value of gradation value is 511. In general, the granularity is high (coarse) if a radiation dose is low and is low (smooth) if a radiation dose is high. Therefore, it can be said that the better image quality is obtained as the granularity becomes lower. A Wiener spectrum may be mentioned as a specific example of granularity. As the image quality evaluation value, not only the granularity but also contrast and sharpness may be adopted. It can be said that the better image quality is obtained as these values become higher.

The storage processing unit 31 executes processing for storing the X-ray image 15 and the radiographing information 16 from the client terminal 18 of each medical facility 11, which have been received through the communication I/F 23S, and the granularity derived by the image analysis unit 30 in the storage device 22S (an aspect of a storage unit) so as to be associated with each other. The storage processing unit 31 associates the X-ray image 15, the radiographing information 16, and the granularity with each other using a common serial number. These may also be associated with each other by storing the radiographing information 16 or the granularity in the DICOM tags of the X-ray image 15, for example.

In response to a request of transmission of the statistical data 17 from the client terminal 18 to which the target radiographing information 16 of the statistical data 17 and the search conditions of granularity are given, the search processing unit 32 searches for and extracts the radiographing information 16 matched with the designated search conditions and the granularity associated therewith from the storage device 22S. The radiographing information 16 and granularity of the medical facility 11, in which the client terminal 18 that has transmitted the transmission request is present, are also included in objects to be searched for by the search processing unit 32. The search processing unit 32 transmits the extracted radiographing information 16 and granularity to the statistical data generation unit 33.

Figure 5:
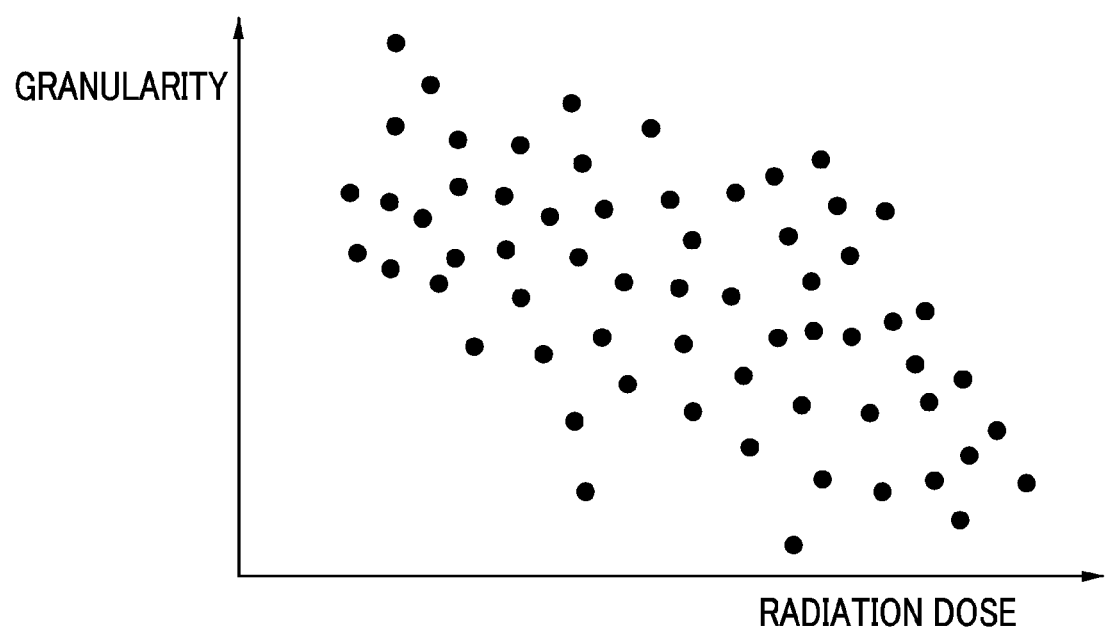
FIG. 5 is a graph showing statistical data.

The statistical data generation unit 33 generates statistical data based on the radiographing information 16 and the granularity from the search processing unit 32. Specifically, a scatter plot shown in FIG. 5 is generated as the statistical data 17. In the scatter plot, a radiation dose of the radiographing information 16 is shown on the horizontal axis, and the granularity is shown on the vertical axis.

In the medical facility 11 actively engaged in low-dose radiographing, efforts to reduce the radiation dose are made by changing the radiographing conditions and an increase of the granularity is suppressed in order not to degrade the quality of the X-ray image 15. For this reason, such medical facilities 11 are plotted in the lower left region of the scatter plot shown in FIG. 5. In contrast, the medical facilities 11 which are not eager for low-dose radiographing are plotted in the upper right region of the scatter plot. In addition, if the points in the scatter plot are discrete, it can be seen that attitudes toward low-dose radiographing of the respective medical facilities 11 are not consistent and efforts for low-dose radiographing have not been made. In contrast, if the points of the scatter plot are gathered near the lower left region of the scatter plot, it can be seen that the low-dose radiographing is realized since radiographing is performed in the ideal radiographing conditions in each medical facility 11.

In addition, in FIG. 5, when there is a point in a lower direction (in a direction in which the granularity decreases) from the point plotted for a own facility (medical facility 11 which owns the client terminal 18 that has transmitted a transmission request), the granularity can be reduced while maintaining the radiation dose if the radiographing conditions of the medical facility 11 of the point are used. In addition, when there is a point in a left direction (in a direction in which the radiation dose decreases) from the point plotted for the own facility, the radiation dose can be reduced while maintaining the granularity if the radiographing conditions of the medical facility 11 of the point are used. Thus, according to the scatter plot shown in FIG. 5, various kinds of information useful for low-dose radiographing can be read immediately as shown above.

The statistical data generation unit 33 transmits the generated statistical data 17 and the radiographing information 16, which has been used to generate the statistical data 17, to the communication I/F 23S. The communication I/F 23S transmits the radiographing information 16 and the statistical data 17 to the client terminal 18 that has transmitted a transmission request.

Figure 6:
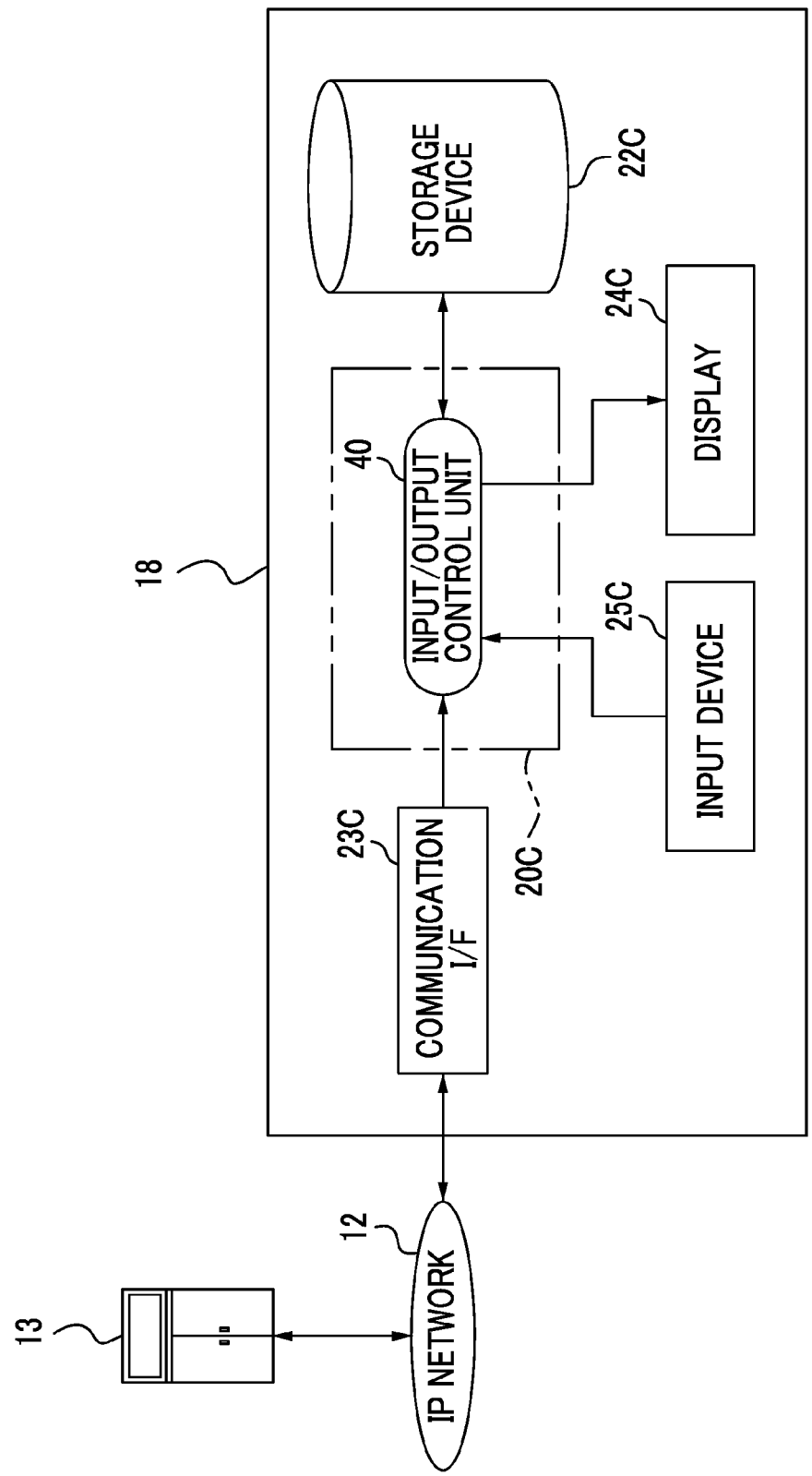
FIG. 6 is a block diagram showing the internal configuration of a client terminal.

In FIG. 6, when a client program starts, the CPU 20C of the client terminal 18 functions as an input/output control unit 40. The input/output control unit 40 reads screen data according to the operation of the input device 25C from the storage device 22C and outputs various operation screens to the display 24C based on the read screen data. The input/output control unit 40 receives the input of an operation instruction from the input device 25C through a GUI disposed on the operation screen.

Figure 7:
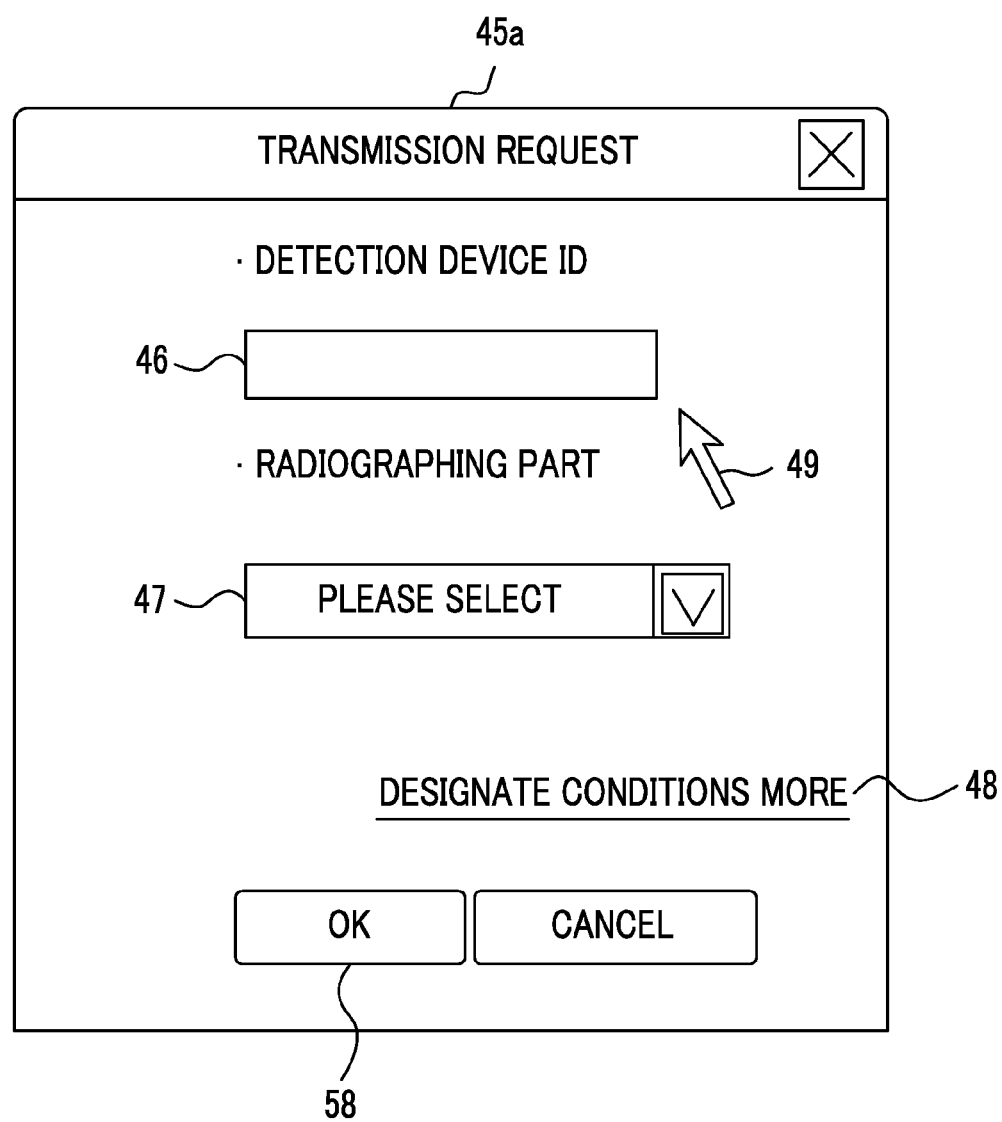
FIG. 7 is a diagram showing a transmission request window.

The input/output control unit 40 displays a transmission request window 45a shown in FIG. 7 on the display 24C when the operator of the client terminal 18 requests the central server 13 to transmit the statistical data 17. An input box 46 for inputting a detection device ID, which is to be searched for, of the radiographing information 16 and a pull-down menu 47 for selecting a radiographing part are displayed as a GUI in the transmission request window 45a.

Figure 8:
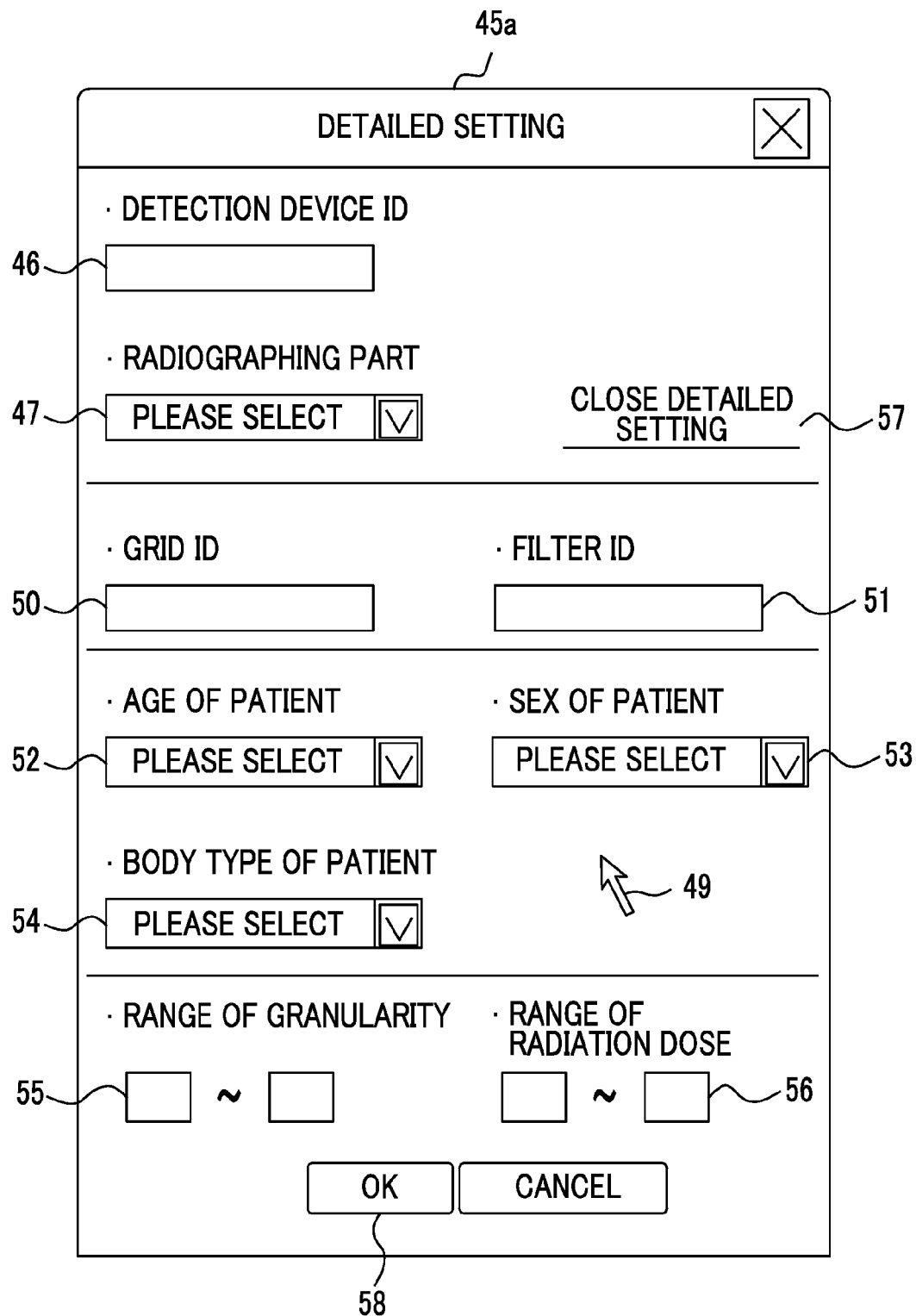
FIG. 8 is a diagram showing a transmission request window.

A link 48 is disposed in the transmission request window 45a. The link 48 is clicked with a cursor 49 of a mouse when search conditions need to be further added in addition to the detection device ID and the radiographing part. When the link 48 is clicked, the input/output control unit 40 displays a transmission request window 45b shown in FIG. 8 on the display 24C. Not only the input box 46 and the pull-down menu 47 of the transmission request window 45a but also input boxes 50 and 51 for inputting a grid ID and a filter ID, pull-down menus 52, 53, and 54 for selecting the patient age, sex and body type, input boxes 55 and 56 for inputting the ranges of granularity and radiation dose, and a link 57 for returning the transmission request window 45*b* to the transmission request window 45*a* are provided in the transmission request window 45*b*.

The operator performs keyboard input of a detection device ID by moving the cursor 49 of the mouse to the input box 46, selects a desired radiographing part by clicking the pull-down menu 47 with the cursor 49, clicks the link 48 when necessary in order to input and select other search conditions, and then clicks an OK button 58 with the cursor 49. The input/output control unit 40 transmits the search conditions input when the OK button 58 is clicked, as a transmission request, from the communication I/F 23C to the central server 13.

In addition, input of the conditions of the detection device ID and the radiographing part may be essential, and input of the other conditions displayed in the transmission request window 45*b* may be optional. In addition, search may be possible if only one item is input with all conditions optional. In addition, the range of search may be narrowed down to the own facility or radiographing date and time of last one month, or a specific radiographer may be designated. The search conditions are not limited to those mentioned in this example.

Figure 9:
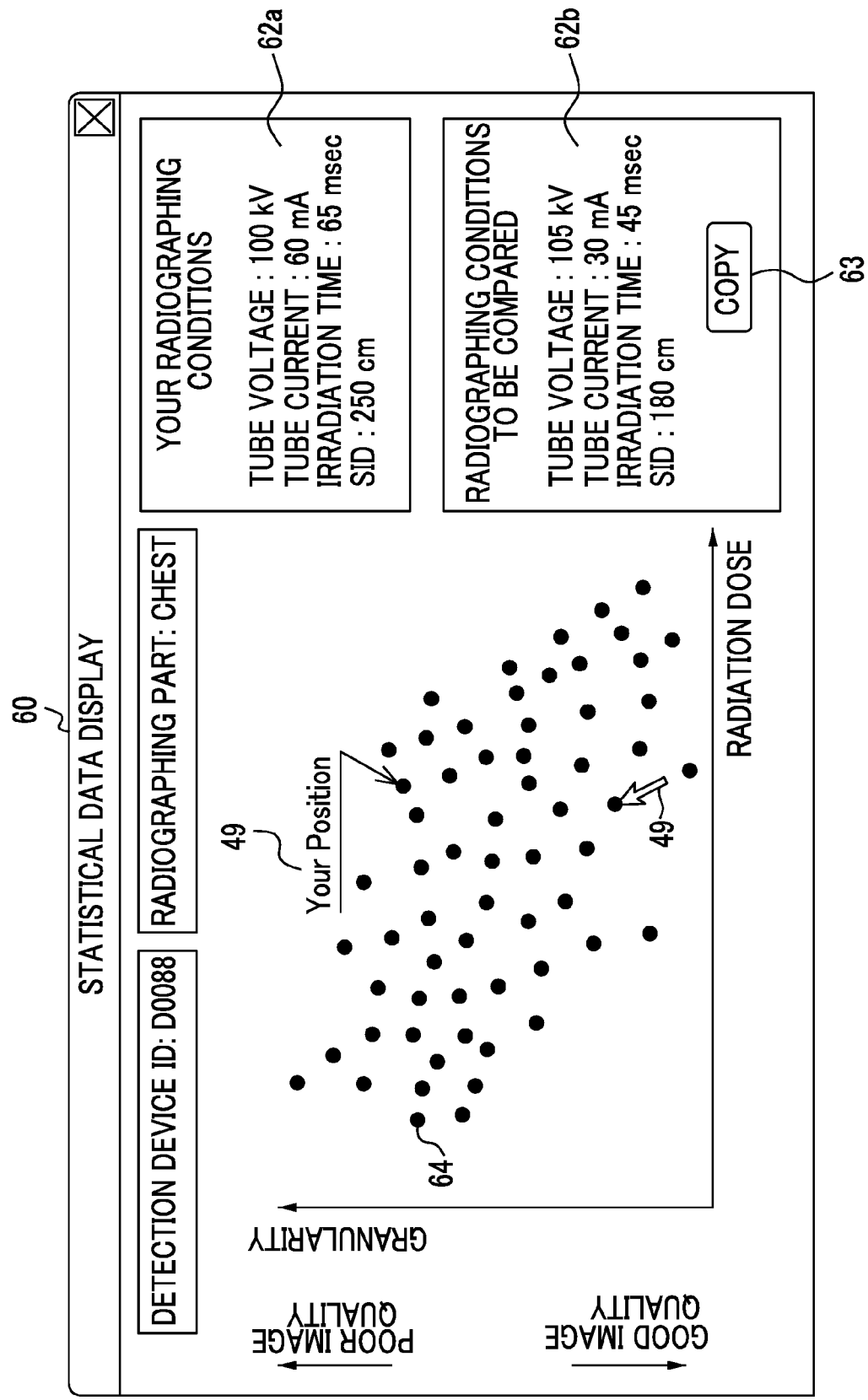
FIG. 9 is a diagram showing a statistical data display window.

When the statistical data 17 from the central server 13 is received through the communication I/F 23C, the input/output control unit 40 displays a statistical data display window 60 shown in FIG. 9 on the display 24C. A detection device ID and a radiographing part (in this example, "D0088" and "chest") designated in the transmission request and a scatter plot, which is the statistical data 17, are displayed in the statistical data display window 60. When other search conditions are input in the transmission request window 45*b*, the search conditions are also displayed together with the detection device ID and the radiographing part. The arrow and "Your Position" indicated by reference numeral 61 show a point of the medical facility 11 where the client terminal 18 that has transmitted a transmission request is present. When the radiographing information 16 and granularity of the medical facility 11 where the client terminal 18 that has transmitted a transmission request is present are not searched by the search processing unit 32 and there is no point on the scatter plot, naturally there is no display of reference numeral 61.

A region 62*a*, which displays radiographing conditions (tube voltage, tube current, irradiation time, and SID) of the medical facility 11 where the client terminal 18 that has transmitted a transmission request is present, and a region 62*b*, which displays radiographing conditions of the medical facility 11 to be compared with the medical facility 11 where the client terminal 18 that has transmitted a transmission request is present, are provided in the statistical data display window 60. The radiographing conditions of the medical facility 11 where the client terminal 18 that has transmitted a transmission request is present are always displayed in the region 62*a*. On the other hand, the radiographing conditions of the medical facility 11 of the point indicated by the cursor 49 are displayed in the region 62*b*. Display of the radiographing conditions of the region 62*b* is switched each time the cursor 49 is moved to another point. The input/output control unit 40 displays the region 62*b* based on the items of the radiographing conditions of the radiographing information 16 received together with the statistical data 17. In addition, a grid ID and a filter ID may be added to the information displayed in the regions 62*a* and 62*b*.

The operator can view the statistical data display window 60, move the cursor 49 to a desired point to compare the regions 62*a* and 62*b* with each other, and examine how to change the radiographing conditions of the own facility to achieve low-dose radiographing or high image quality. For example, if the point of the reference numeral 61 is compared with the point indicated by the cursor 49, both radiation doses are approximately the same, but the granularity of the latter point (cursor 49) is low and the image quality is good accordingly. Accordingly, the radiographing conditions of the latter point (cursor 49) can be referred to as a model of the radiographing conditions for improving the image quality. In addition, in the case of a point 64 on the left side of the point indicated by the reference numeral 61, the image quality is approximately the same as that of the point indicated by the reference numeral 61, but the radiation dose is lower than that of the point indicated by the reference numeral 61. Accordingly, the radiographing conditions of the point 64 can be referred to as a model for low-dose radiographing.

When a certain point is clicked with the cursor 49, the display of the region 62*b* is fixed to the radiographing conditions of the medical facility 11 at the point. At this time, the input/output control unit 40 causes a copy button 63 to appear in the region 62*b*. When the copy button 63 is clicked with the cursor 49, information of the radiographing conditions displayed in the region 62*b* is transmitted to the X-ray radiographing system 14 and is copied. As a result, the X-ray radiographing system 14 performs radiographing in the copied radiographing conditions in the next X-ray radiographing in which the detection device ID is "D0088" and the radiographing part is a "chest". In addition, in order to cancel the fixation of the radiographing conditions, a certain point is clicked with the cursor 49 once again.

Figure 10:
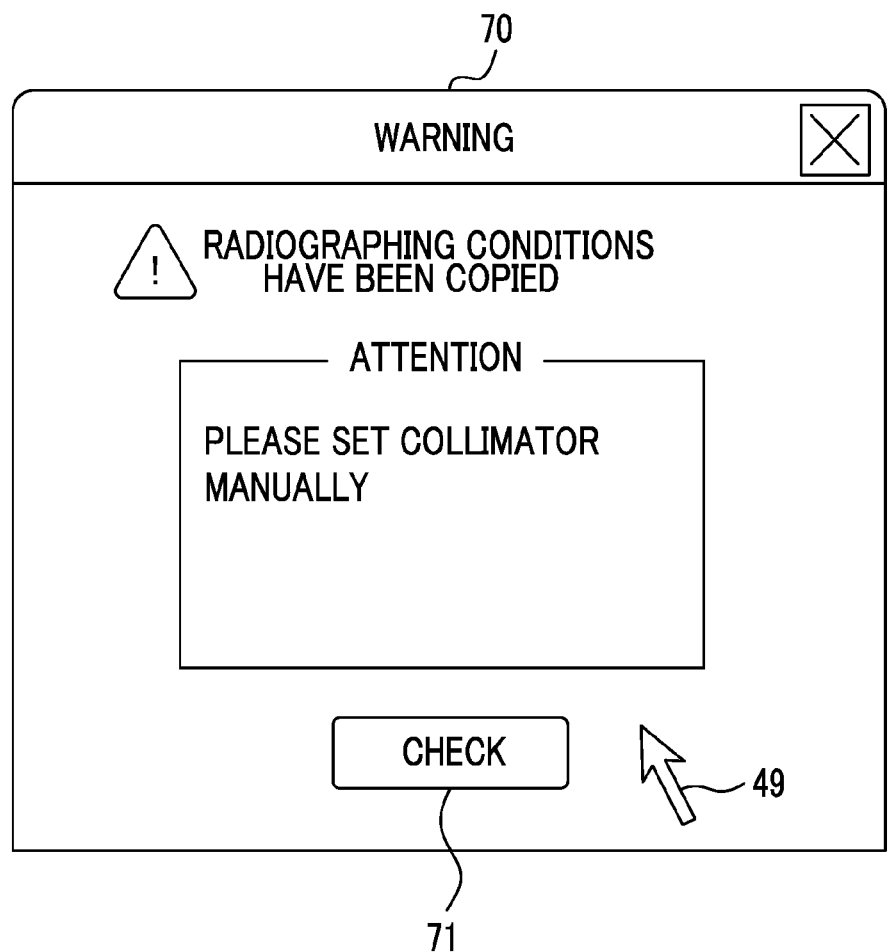
FIG. 10 is a diagram showing a warning display window.

When system information of the radiographing information 16 of the copy location of which radiographing conditions are to be copied is different from the system information of the X-ray radiographing system 14 of the own facility (copy receiving side), the input/output control unit 40 displays on the display 24C a warning display window 70 shown in FIG. 10 after the copy button 63 is clicked. In this example, a case is shown in which a collimator item of the system information of the copy location, of which radiographing conditions are to be copied, is set as "Automatic" and the collimator item of the system information of the X-ray radiographing system 14 of the own facility is set as "manual" which is different from that in the radiographing condition copy location. Accordingly, a message prompting the manual setting of the collimator is displayed. When filter settings are different as automatic and manual or when grid IDs or filter IDs are different, messages corresponding to these are displayed. The input/output control unit 40 closes the warning display window 70 when a check button 71 is clicked with the cursor 49.

Figure 11:
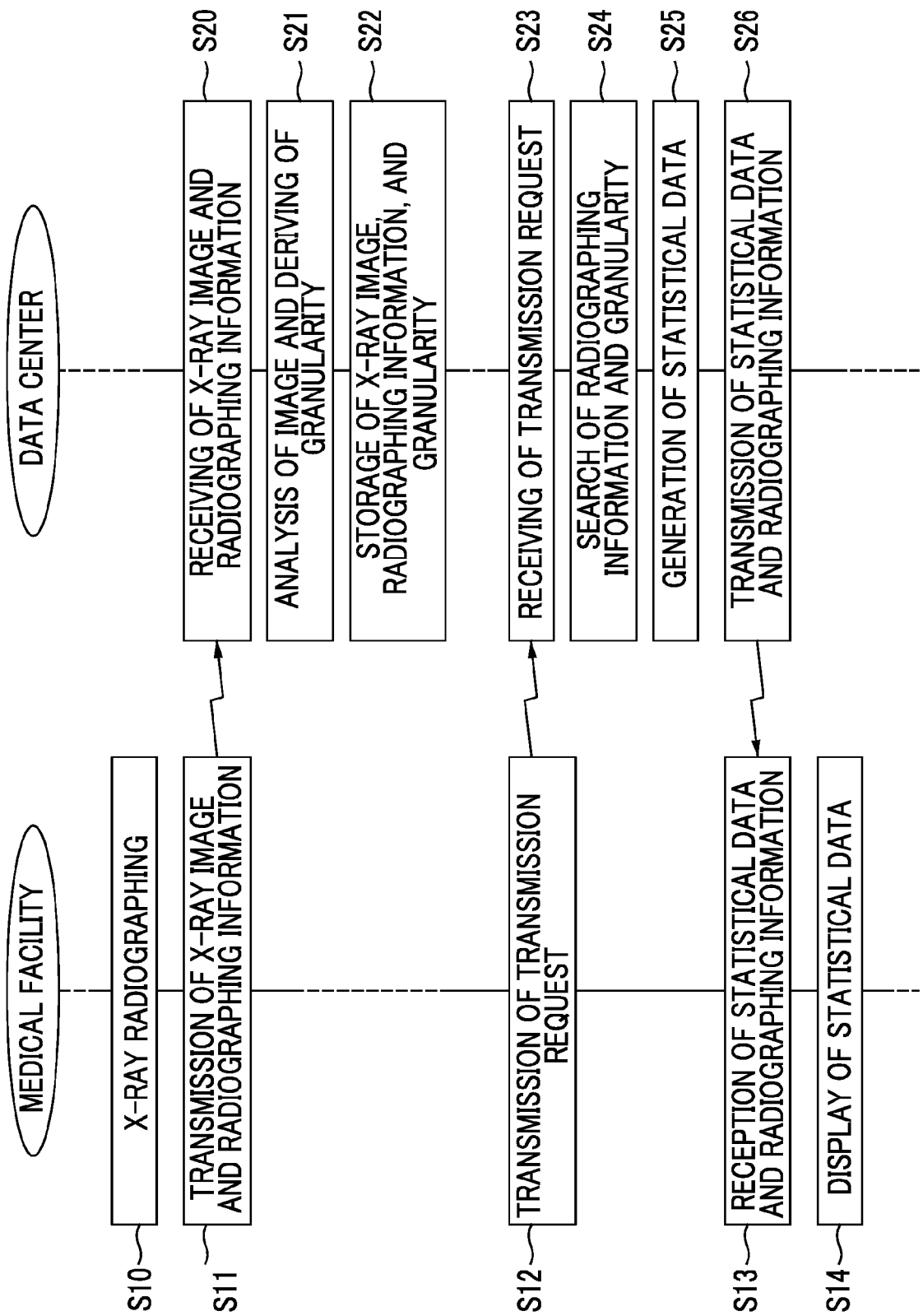
FIG. 11 is a flow chart showing the flow of the process of the X-ray radiographing information management system.

Hereinafter, the operation based on the above configuration will be described with reference to the flow chart shown in FIG. 11. First, in the medical facility 11, X-ray radiographing is performed using the X-ray radiographing system 14 (S10 (step 10)). The X-ray image 15 and the radiographing information 16 at this time are transmitted and received between the communication I/F 23C of the client terminal 18 and the communication I/F 23S of the central server 13 (S 11 and S20). In the central server 13, the X-ray image 15 received through the communication I/F 23S is transmitted to the image analysis unit 30, and the image analysis unit 30 derives the granularity of the region of interest of the X-ray image 15 (S21). Then, the storage processing unit 31 stores the granularity, the X-ray image 15, and the radiographing information 16 in the storage device 22S so as to be associated with each other (S22).

A transmission request of the statistical data 17 is made through the transmission request windows 45*a* and 45*b* in the client terminal 18, and this transmission request is transmitted and received between the communication I/F 23C of the client terminal 18 and the communication I/F 23S of the central server 13 (S12 and S23).

In the central server 13, the search processing unit 32 searches for and extracts the radiographing information 16 and the granularity matched with the search conditions designated in the transmission request (S24). Then, the statistical data generation unit 33 generates a scatter plot as the statistical data 17 based on the search result of the search processing unit 32 (S25), and this scatter plot and the radiographing information 16 are transmitted and received between the communication I/F 23S and the communication I/F 23C (S13 and S26). In the client terminal 18, the input/output control unit 40 displays the statistical data display window 60 on the display 24C based on the statistical data 17 received through the communication I/F 23C (S14).

The operator of the client terminal 18 views the statistical data display window 60 on the display 24C. The content of the statistical data display window 60 may be printed by a printer, or may be stored in the storage device 22C. In this manner, the statistical data 17 may be used as reference material for a change to the radiographing conditions for low-dose radiographing, or may be used as material for informed consent of a patient.

In addition, the operator moves the cursor 49 to the point of the statistical data 17 in the statistical data display window 60 to display the radiographing conditions of the medical facility 11 of the point in the region 62b, and compares the radiographing conditions of the medical facility 11 of the point in the region 62b with the radiographing conditions of the own facility displayed in the region 62a in order to achieve low-dose radiographing and high image quality. When the operator wants to copy the radiographing conditions, the operator clicks a desired point with the cursor 49 to cause the copy button 63 to appear in the region 62b, and clicks the copy button 63 with the cursor 49. Then, the radiographing conditions of the point are copied to the X-ray radiographing system 14, and X-ray radiographing is subsequently performed in the copied radiographing conditions. When system information of the radiographing information 16 of the copy location of which radiographing conditions are to be copied is different from the system information of the X-ray radiographing system 14 of the own facility, the input/output control unit 40 displays the warning display window 70 on the display 24C.

As described above, according to the present invention, the central server 13 generates a scatter plot, which has a radiation dose on the horizontal axis and granularity on the vertical axis, as the statistical data 17, transmits the scatter plot to the client terminal 18 and displays it. This helps make a future policy for low-dose radiographing and high image quality. Specifically, when a scatter plot is used as a display form, the relationship between the own facility and other facilities can be easily determined intuitively, compared with a case where display is performed in a list form. In this case, therefore, a future policy for low-dose radiographing and high image quality can be quickly made. In addition, referring to and copying the wrong radiographing conditions, which are not effective for low-dose radiographing and high image quality, can also be prevented.

Since the radiographing conditions of the own facility and other facilities are displayed in the regions 62a and 62b, respectively, comparison is easy.

Since the radiographing conditions can be copied, operability and convenience can be improved. In addition, since a warning display is given when the system information of the radiographing information 16 of the copy location, of which radiographing conditions are to be copied, is different from the system information of the X-ray radiographing system 14 of the own facility, a mistake, such as forgetting to set a collimator, can be prevented.

In addition, the warning display window 70 may be displayed on a display of a control device of the X-ray radiographing system 14 instead of the display 24C of the client terminal 18, and the warning display method is not limited to the embodiment described above. In addition, instead of copying the radiographing conditions as they are, the operator may set the radiographing conditions manually by performing fine adjustment of the values of the tube voltage and the like with reference to the radiographing conditions used as a model.

Figure 12:
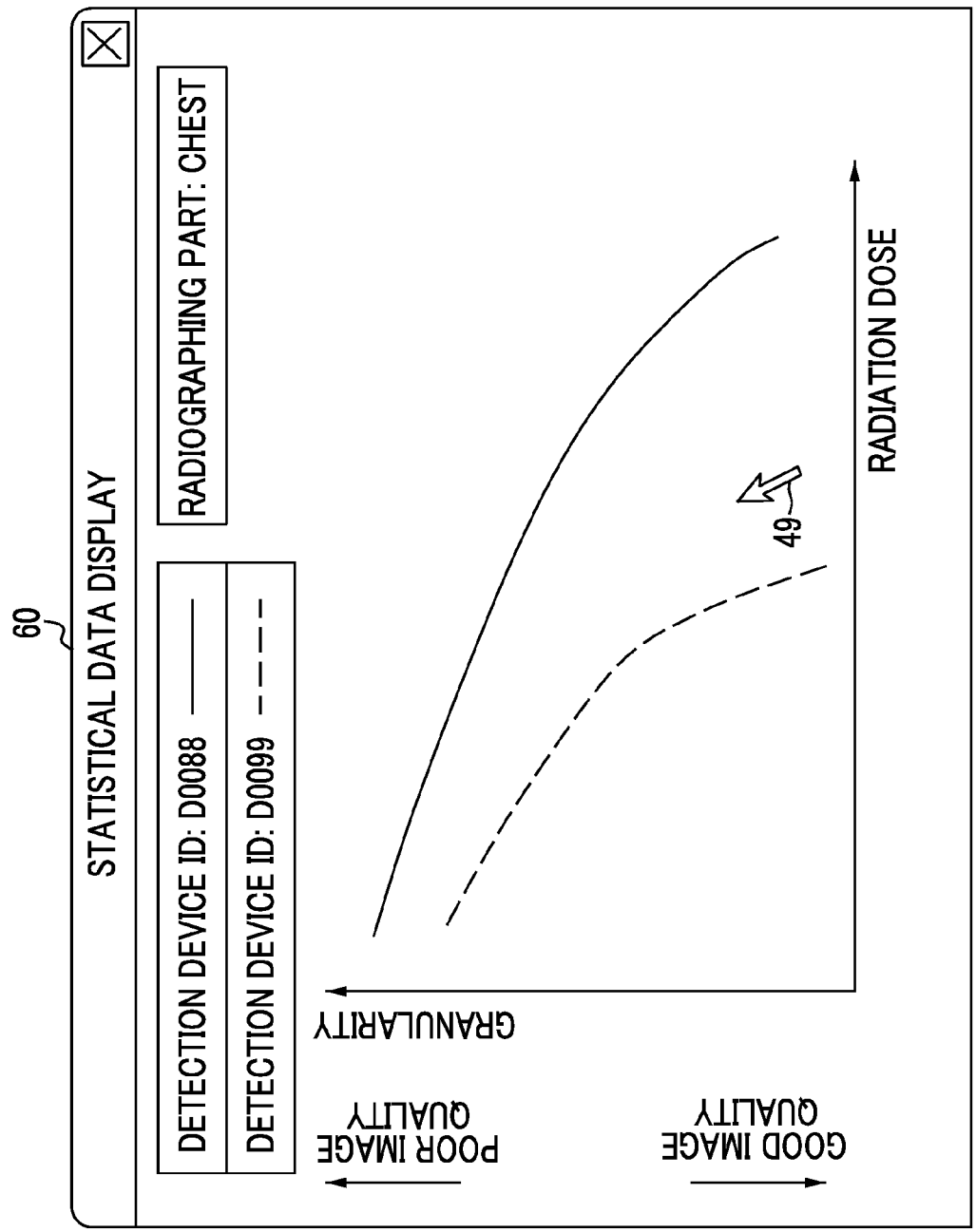
FIG. 12 is a diagram showing the statistical data display window when a plurality of X-ray image detection devices are designated as search conditions.

Although a single X-ray image detection device is targeted in the above embodiment, detection device IDs of a plurality of X-ray image detection devices may be designated in the transmission request, and statistical data regarding a plurality of X-ray image detection devices may be acquired by a single transmission request. In this case, as shown in FIG. 12, if the statistical data of the plurality of X-ray image detection devices (detection device ID "D0088" shown by the solid line and detection device ID "D0099" shown by the dotted line) is displayed together in the statistical data display window 60 so that the statistical data can be compared with each other, the superiority of the X-ray image detection devices is self-explanatory. In this example, it can be seen that the detection device ID "D0099" can perform high-quality X-ray radiographing with a low radiation dose compared with the detection device ID "D0088". In this case, however, it may be difficult to know which point corresponds to which X-ray image detection device in the scatter plot. Therefore, the statistical data generation unit 33 calculates an approximated curve of the scatter plot of each X-ray image detection device, and this approximated curve is displayed instead of the scatter plot.

In addition, one or more radiographer IDs may be designated instead of the detection device ID in the search conditions, and the statistical data 17 of a specific radiographer may be generated. The habit when a radiographer sets radiographing conditions can be recognized. Accordingly, recommendations for a radiographer which is not able to realize low-dose radiographing can be given by making the radiographer view the radiographing conditions of a radiographer who is able to realize low-dose radiographing.

Contrary to the embodiment described above, a scatter plot having a radiation dose on the vertical axis and granularity on the horizontal axis may be set as the statistical data 17. In addition, when not only the granularity but also the contrast, sharpness, and the like are adopted as image quality evaluation values, for example, a three-dimensional contour plot having granularity on the Z axis, contrast or sharpness on the Y axis, and a radiation dose on the X axis may be generated as the statistical data 17 instead of a scatter plot.

In the embodiment described above, the item of system information is prepared in the radiographing information 16. However, since the system information does not change frequently, it is preferable to transmit the system information to the central server 13 and store it in the central server 13 in advance together with the system ID and to set the item of the system ID in the radiographing information 16.

In the above embodiment, the X-ray radiographing information management system 2 configured to include the data center 10 and a plurality of medical facilities 11 has been illustrated. However, these may also be provided in one medical facility as an X-ray radiographing information management system 75 shown in FIG. 13.

In FIG. 13, the X-ray radiographing information management system 75 has a configuration in which a plurality of X-ray radiographing systems 14a, 14b, . . . placed in a plurality of radiographing rooms A, B, . . . of the medical facility, a client terminal 18, and an X-ray radiographing information management apparatus 76 are connected to each other through a LAN 77 provided in the medical facility. The X-ray radiographing information management apparatus 76 corresponds to the central server 13 in the embodiment described above.

In this case, a radiographing room ID may be added to the items of the radiographing information instead of the medical facility ID. Each point of the scatter plot becomes each radiographing room or each radiographer. The achievement situation of low-dose radiographing can be checked in units of a radiographing room or a radiographer.

In the above embodiment, the radiation dose detected by the dose detection sensor of the X-ray radiographing system 14 has been described as an example. However, the radiation dose may be calculated using an area dose calculation expression based on the NDD method (Numerical Dose Determination method), for example. Alternatively, instead of the radiation dose itself, an amount equivalent to the radiation dose, for example, a tube current irradiation time product (mAs value) or a reading sensitivity value (S value), which is obtained by analyzing an X-ray image using a histogram, may also be used. The mAs value may be calculated from the tube current and irradiation time of the radiographing conditions. When the S value is used, the image analysis unit 30 is made to have a function of calculating the S value from the X-ray image data. If only the X-ray image data is present, the S value can be calculated even if there are no radiographing conditions. Accordingly, the S value is preferably used when the radiographing conditions are not included in the radiographing information. However, since the definition of the S value changes slightly depending on the manufacturer, the S value is corrected and standardized to become a uniform value irrespective of the manufacturer.

In general, in the X-ray radiographing, radiographing conditions of the preset value stored in advance are set, and a radiographer adjusts the preset value when necessary. For this reason, it is preferable that the radiographing conditions of the value, which is finally set and is used in actual X-ray radiographing, be stored in the radiographing information. However, when strict accuracy is not required, for example, when the radiographing conditions are viewed for reference, a preset value may be stored.

The function of the statistical data generation unit may be added to the client terminal. In this case, search results of the search processing unit are transmitted from the central server or the X-ray radiographing information management apparatus to the client terminal. In addition, a client terminal to transmit an X-ray image and radiographing information and a client terminal to receive statistical data may be separate terminals. There may be a plurality of client terminals. In short, units of the present invention may be separately provided in a plurality of apparatuses. Alternatively, as in the embodiment described above, the client terminal may have a function of only the display unit, and the central server or the X-ray radiographing information management apparatus may have functions of other units.

In addition, the present invention may also be applied to the radiographing information management of a radiographing system that uses other radiations, such as y-rays, without being limited to the X-rays.

What is claimed is:

1. A radiographing information management system comprising:
   an image analysis unit that analyzes a radiological image, which is obtained by a radiographing system, to derive an image quality evaluation value indicating quality of the image;
   a storage processing unit that stores the image quality evaluation value derived by the image analysis unit and radiographing information, which includes an item of a radiation dose or an equivalent amount equivalent to the radiation dose, in a storage unit so as to be associated with each other;
   a search unit that searches for radiographing information, which has an item designated in search conditions, and an image quality evaluation value, which is associated with the radiographing information, from the storage unit;
   a statistical data generation unit that generates statistical data, which has an image quality evaluation value and a radiation dose or an equivalent amount as parameters, based on the radiographing information and the image quality evaluation value associated with the radiographing information that have been searched for by the search unit; and
   a display unit that displays the statistical data generated by the statistical data generation unit,
   wherein the image quality evaluation value is granularity of a region of interest of a radiological image.

2. The radiographing information management system according to claim 1,
   wherein the radiographing information includes any one of a medical facility in which a radiographing system is placed, a radiographer in charge of radiographing, and a radiographing room where radiographing is performed, and
   the statistical data generation unit generates a scatter plot including a set of points, which indicates a relationship between the image quality evaluation value and the radiation dose or the equivalent amount for each medical facility, each radiographer, or each radiographing room, as the statistical data.

3. The radiographing information management system according to claim 1,
   wherein the radiographing information includes an item of information of a patient, who has been subject to radiographing, and this information is designated as search conditions.

4. The radiographing information management system according to claim 3, wherein the patient information includes any one of age, sex, and body type.

5. The radiographing information management system according to claim 1, wherein the radiographing information includes an item of information of the radiographing system, and this information is designated as search conditions.

6. The radiographing information management system according to claim 5, wherein the information of the radiographing system includes IDs for uniquely identifying a radiological image detection device, a grid, and a filter, and information indicating whether settings of a collimator and a filter are automatic or manual.

7. The radiographing information management system according to claim 6,
   wherein, when IDs of a plurality of radiological image detection devices are designated as the search conditions, the statistical data generation unit generates statistical data of each of the radiological image detection devices, and the display unit displays the statistical data of each radiological image detection devices so as to be compared with each other.

8. The radiographing information management system according to claim 1, wherein the radiographing information includes an item of radiographing conditions, and the item of the radiographing conditions is designated as search conditions.

9. The radiographing information management system according to claim 8, wherein the radiographing conditions include a radiographing part, a tube voltage, a tube current, and irradiation time of a radiation source, and a distance between a radiation source and a radiological image detection device.

10. The radiographing information management system according to claim 8, wherein the display unit displays a plurality of radiographing conditions so as to be compared with each other.

11. The radiographing information management system according to claim 8, wherein the display unit displays radiographing conditions so as to be linked to statistical data.

12. The radiographing information management system according to claim 8, wherein the display unit displays a GUI for copying radiographing conditions.

13. The radiographing information management system according to claim 12, further comprising:

a warning display unit that, when system information of radiographing information of a copy location having the copied radiographing conditions is different from system information of radiographing information of a copy receiving side, displays this situation.

14. A radiographing information management method comprising:

an image analysis step of analyzing a radiological image, which is obtained by a radiographing system, to derive an image quality evaluation value using an image analysis unit;

a storage processing step of storing the image quality evaluation value derived in the image analysis step, and radiographing information, which includes an item of a radiation dose or an equivalent amount equivalent to the radiation dose, in a storage unit so as to be associated with each other using a storage processing unit;

a search step of searching for the radiographing information, which has an item designated in search conditions, and an image quality evaluation value, which is associated with the radiographing information, from the storage unit using a search unit;

a statistical data generation step of generating statistical data, which has an image quality evaluation value and a radiation dose or an equivalent amount as parameters, based on the radiographing information and the image quality evaluation value associated with the radiographing information, which have been searched for in the search step, using a statistical data generation unit; and a display step of displaying the statistical data generated in the statistical data generation step on a display unit, wherein the image quality evaluation value is granularity of a region of interest of a radiological image.

15. A non-transitory computer-readable recording medium that records a radiographing information management program causing a computer to realize:

an image analysis function of analyzing a radiological image, which is obtained by a radiographing system, to derive an image quality evaluation value;

a storage processing function of storing the image quality evaluation value derived by the image analysis function and radiographing information, which includes an item of a radiation dose or an equivalent amount equivalent to the radiation dose, in a storage unit so as to be associated with each other;

a search function of searching for the radiographing information, which has an item designated in search conditions, and an image quality evaluation value, which is associated with the radiographing information, from the storage unit;

a statistical data generation function of generating statistical data, which has an image quality evaluation value and a radiation dose or an equivalent amount as parameters, based on the radiographing information and the image quality evaluation value associated with the radiographing information that have been searched for by the search function; and a display function of displaying the statistical data generated by the statistical data generation function, wherein the image quality evaluation value is granularity of a region of interest of a radiological image.

* * * * *